(12) United States Patent
Westbye

(10) Patent No.: US 7,682,343 B2
(45) Date of Patent: Mar. 23, 2010

(54) SYRINGE WITH ANTI-ROTATION FOR LUER LOCK

(75) Inventor: Lars Tommy Westbye, Carlsbad, CA (US)

(73) Assignee: Safety Syringes, Inc., Carlsbad, CA (US)

( * ) Notice: Subject to any disclaimer, the term of this patent is extended or adjusted under 35 U.S.C. 154(b) by 126 days.

(21) Appl. No.: 11/697,259

(22) Filed: Apr. 5, 2007

(65) Prior Publication Data

US 2007/0185459 A1 Aug. 9, 2007

Related U.S. Application Data

(63) Continuation of application No. 10/977,209, filed on Oct. 29, 2004, now Pat. No. 7,255,689.

(51) Int. Cl.
A61M 5/32 (2006.01)
A61M 5/00 (2006.01)

(52) U.S. Cl. .................. 604/192; 604/198; 604/263

(58) Field of Classification Search .................. 604/192
See application file for complete search history.

(56) References Cited

U.S. PATENT DOCUMENTS 4,840,619 A 6/1989 Hughes
5,389,085 A 2/1995 D'Allessio et al.
6,319,234 B1 11/2001 Restelli et al.
6,485,469 B1 11/2002 Stewart et al.
6,613,022 B1 9/2003 Doyle
6,623,459 B1 9/2003 Doyle
6,976,976 B2 * 12/2005 Doyle .................. 604/198

FOREIGN PATENT DOCUMENTS

EP 0 680 767 A1 11/1995
WO WO 2004052432 A2 * 6/2004

* cited by examiner

*Primary Examiner*—Nicholas D Lucchesi
*Assistant Examiner*—Jason Flick
(74) *Attorney, Agent, or Firm*—Orrick, Herrington & Sutcliffe LLP

(57) ABSTRACT

A needle guard for a syringe including tabs and preferably springboards disposed on the needle guard configured to engage a luer lock to prevent rotation of the luer lock during needle exchange. The body of the needle guard preferably includes springboards which are in communication with tabs disposed on the shield when the shield is in a first, retracted position. Inward or radial depression of the tabs forces the springboards to contact the luer lock and prevent rotation of the luer lock. The needle guard further comprises a slot disposed near the proximal end of the shield which is configured to engage an end tab disposed near the distal end of the body. When the needle guard is activated, the shield slides to a second, extended position and the end tab enters into the slot to lock the shield in the extended position.

5 Claims, 3 Drawing Sheets

SYRINGE WITH ANTI-ROTATION FOR LUER LOCK

CROSS-REFERENCE TO RELATED APPLICATIONS

This application is a continuation of application Ser. No. 10/977,209 filed Oct. 29, 2004, now U.S. Pat. No. 7,255,689, the disclosure of which is incorporated herein by reference.

FIELD OF THE INVENTION

The invention relates generally to syringe systems which include a passive needle guard. More specifically, this invention relates to syringe systems, including a passive needle guard, which also include one or more tabs disposed on the passive needle guard configured to prevent rotation of the syringe during attachment or disengagement of a needle into a lock such as a luer lock.

BACKGROUND OF THE INVENTION

Many current syringe systems include a needle guard coupled with a syringe to reduce the chances of accidental needle sticks and to facilitate safer disposal of the syringe. In general, the needle guard comprises a body and a shield which surround the syringe. Some needle guards further comprise a spring which biases the shield to an extended position when the needle guard is activated. Current needle guards typically inhibit the use of luer locks as connectors for needles to the syringe. A luer lock comprises a threaded attachment connected to the distal, administration end of the syringe. In order to attach a needle to the syringe, a user screws a luer needle having male threads into the female threads of the luer lock. The body and/or shield of current needle guards allow access to the luer lock attached to the syringe via a distal opening, but do not typically allow a user to apply inward or radial pressure on the luer lock during needle exchange. Therefore, in syringe systems which have a needle guard attached, a luer lock may be difficult to use. The needle guard prevents a user from stabilizing the luer lock to restrict rotation of the luer lock during a needle exchange. In current systems, the luer lock rotates in place making needle exchange difficult if not impossible.

SUMMARY OF THE INVENTION

The present invention is directed to a passive needle guard system for use with a syringe having a luer lock. The present invention is also directed at needle guard systems comprising one or more pairs of cooperating tabs or springboards which can be depressed to contact a luer lock to prevent rotation of the luer lock during needle exchange and to methods of making and using such systems. The present invention is further directed to a passive needle guard comprising a tab and slot system which locks the shield of the needle guard in the extended position after the passive needle guard has been activated.

Typically an attached needle guard prevents a user from having access to the luer lock in order to grasp and prevent rotation of the luer lock during needle exchange or insertion. The tab system of the present invention effectively prevents the rotation of the luer lock by contacting tabs disposed on the needle guard with the luer lock during needle exchange. The tabs can then be released, the medication administered, and the needle guard can be activated to cover the needle.

The needle guard of the present invention comprises a body and a shield. The needle guard may further comprise a spring disposed between the body and the shield arranged to bias the shield to the extended position. The body includes a cylindrical opening configured to receive a syringe and a distal opening from which the needle of the syringe extends. The body further comprises a pair of springboards disposed on opposite sides of the distal end of the body.

The shield is slidably attached to the body and has a proximal and distal end. Initially, the shield is held in a first retracted position by cooperating catches disposed on the body and the shield. In this first position, the needle of the syringe extends beyond the shield. During use of the syringe, the needle guard is activated and the shield moves distally to the second, extended position. In the second, extended position, the shield covers the needle of the syringe thereby preventing accidental needle sticks. The distal end of the shield comprises two or more opposing tabs. When the shield is in the first, retracted position, the tabs are configured to engage the springboards when radial or inward pressure is applied to the tabs. Upon application of sufficient inward pressure to the tabs, the springboards contact the luer lock and restrict rotation of the luer lock.

The needle guard of the present invention further comprises a tab and slot system which locks the shield in the extended position after the passive needle guard has been activated. The body comprises a pair of opposing elongate fingers near the distal end of the body. The elongate fingers comprise an end tab disposed at the proximal end of the elongate finger. The shield of the needle guard comprises two opposing slots disposed near the proximal end of the shield configured to receive the end tab of the body. When the needle guard is activated and the shield transitions to the extended position, each end tab on the body enters a cooperating slot on the shield thereby locking the shield in the extended position.

BRIEF DESCRIPTION OF THE DRAWINGS

FIG. 8 is an exploded view of the distal region of a syringe system of the present invention.

DESCRIPTION OF THE PREFERRED EMBODIMENTS

Figure 1:
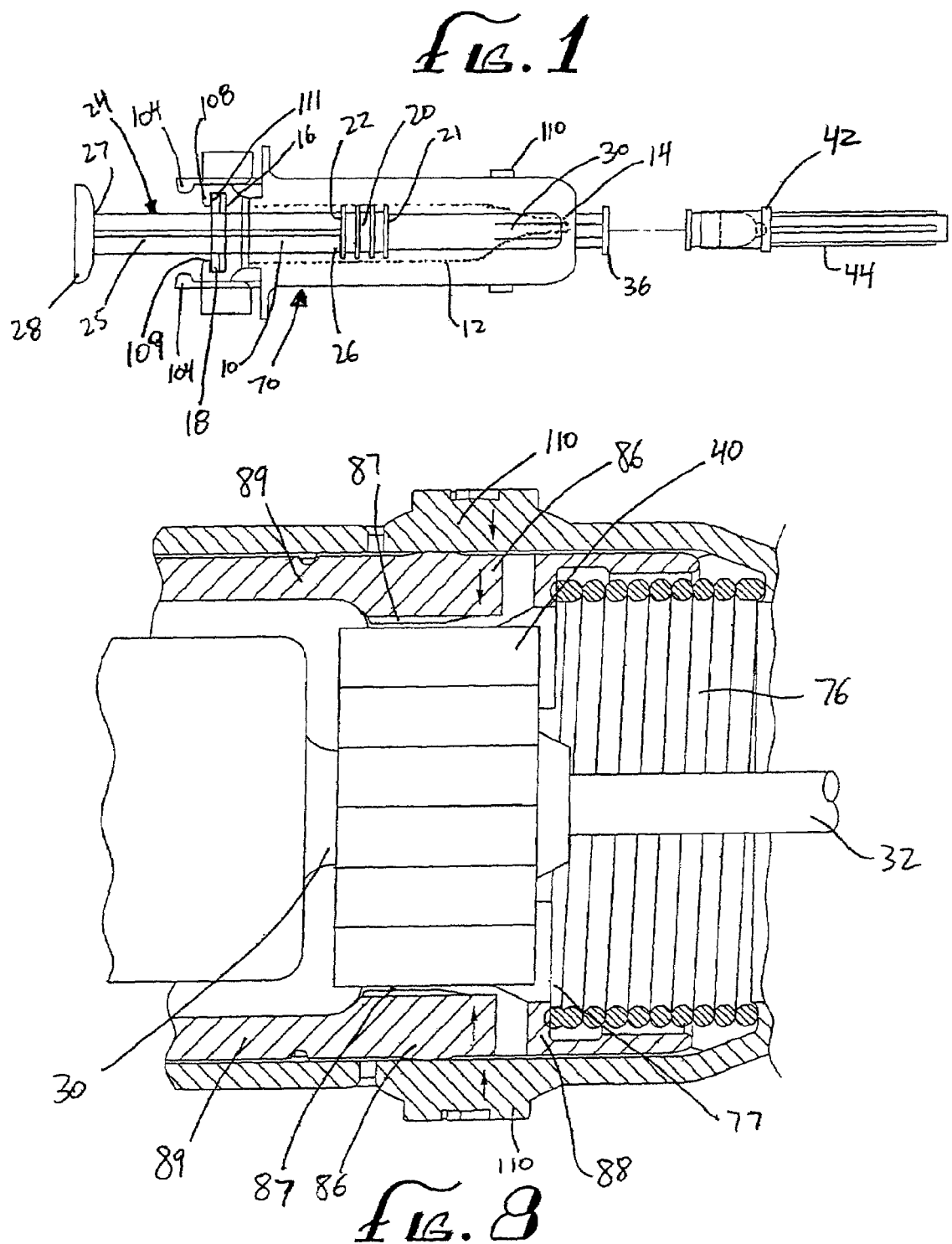
FIG. 1 shows a syringe system of the present invention.

Turning to the drawings, FIG. 1 shows a preferred embodiment of a syringe 10 used in conjunction with the present invention. Preferably, the syringe 10 has a substantially smooth-walled cylindrical barrel 12, a distal end 14 or hub that is the administration end, and a proximal end 16 having a flange 18. The cylindrical barrel 12 typically is manufactured from substantially clear glass. Alternatively, the barrel 12 may be manufactured from plastic such as polypropylene, k-resin, polycarbonate, and the like. The proximal end 16 of the barrel 12 is configured to receive a stopper 20 and a plunger 24 as discussed further below.

The distal end of the cylindrical barrel 12 comprises a needle port 30. The needle port 30 is configured to removably couple a needle 32 (FIG. 8). The needle port 30 may also be configured to receive a syringe cap 36 prior to use of the syringe (FIG. 1). The needle port 30 may be configured to couple with several different sizes of needles 32 having various diameters and lengths. The needles 32 may be connected to the syringe by a luer connector, luer slip, luer, luer lock, or other needle holder as is known in the art. In a preferred embodiment, the needle port 30 comprises a luer slip or luer lock 40 (FIG. 8). The luer lock 40 is configured to allow interchanging of the needle 32 so a user 90 may use the most appropriate needle 32 based on the needs of the patient (not shown). The luer lock 40 comprises a threaded region (not shown) configured to receive the threaded portion (not shown) of a luer needle 42 (FIGS. 1 and 8).

A plunger 24 and a stopper 20 may be inserted into the cylindrical barrel 12 at the proximal end 16 (FIG. 1). The stopper 20 is configured to be slidably coupled into the cylindrical barrel 12 and movable from a proximal position to a distal position. The stopper 20 is preferably made of pliable rubber, thermoplastic rubber, plastic, or similar material. The stopper 20 comprises a distal end 21 and a proximal end 22. The distal end 21 of the stopper 20 is configured to create a seal against the cylindrical barrel 12 of the syringe 10. The proximal end 22 may include threaded layers (not shown). The threaded layers are configured to receive threaded portions (not shown) of a distal region 26 of a stem 25 of the plunger 24. The plunger 24 comprises a stem 25 and a radial element 28 or thumb pad. During operation, the user applies a distal force on the radial element 28 to administer the medication contained in the syringe 10 to the patient.

Figure 7:
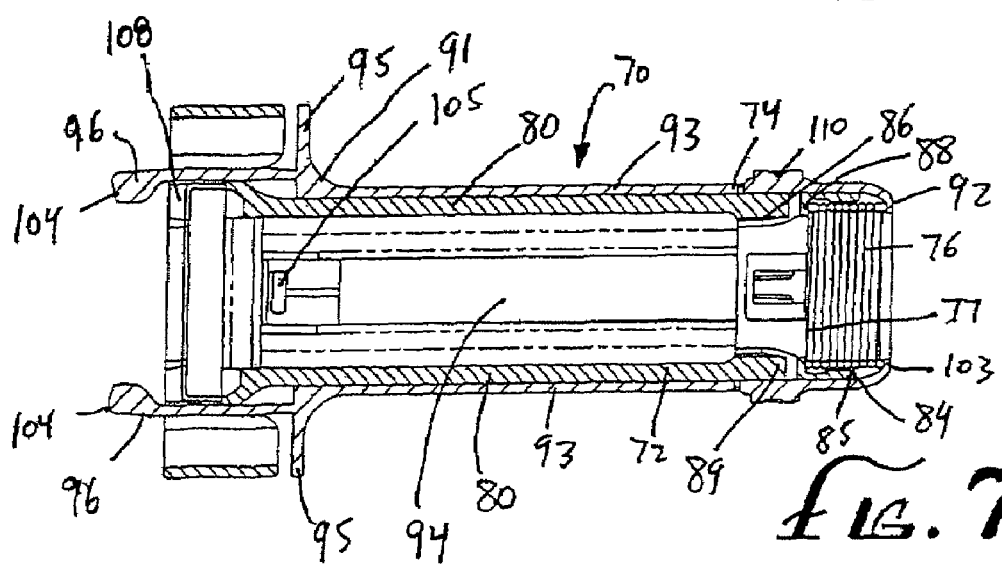
FIG. 7 is a top view of the needle guard of the present invention.

In a preferred embodiment, the syringe 10 is mounted in a needle guard 70 (FIG. 7). The needle guard 70 may be a passive needle guard system such as that disclosed in copending U.S. patent application Ser. No. 09/566,224, filed May 5, 2000, the disclosure of which is incorporated herein by reference. The passive needle guard 70 generally comprises a body 72, a shield 74 and a spring 76. The body 72 of the passive needle guard 70 is configured for receiving and holding the syringe 10. The shield 74 is slidably attached to the body 72. Both the body 72 and the shield 74 are generally molded from plastic, such as polypropylene, k-resin, polycarbonate, or the like. In a preferred embodiment, the body 72 and the shield 74 are substantially clear to facilitate observation of the syringe 10 therein. Alternatively, the body 72 and the shield 74 may be translucent or opaque, and may be colored, such as a latex color, a flesh tone, or a primary color.

Figure 5:
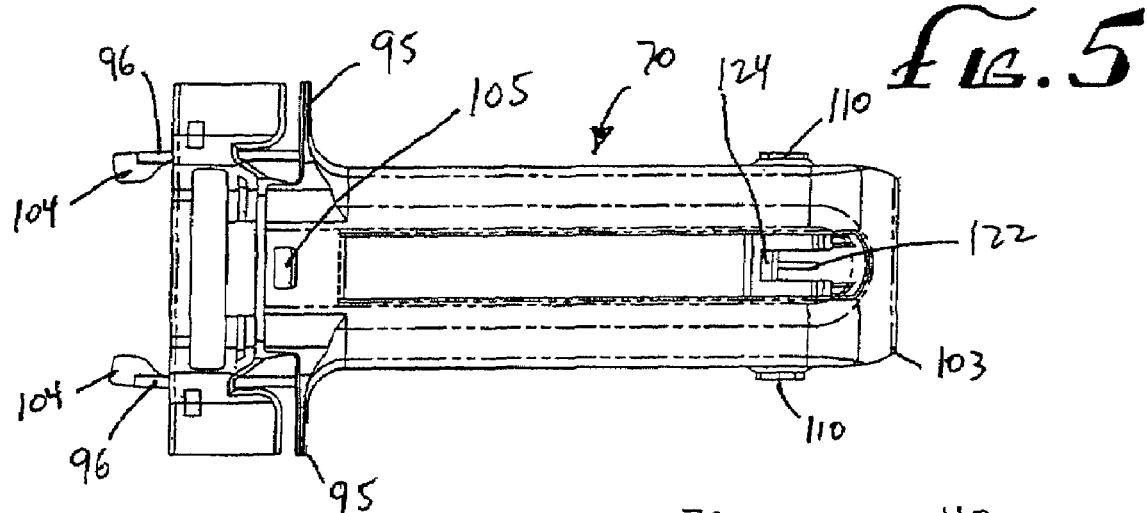
FIG. 5 shows the needle guard of the present invention.

The body 72 may comprise opposing side rails 80 defining two elongate openings or windows (not shown) extending at least partially between a proximal end 83 and a distal end 84 of the body 72 (FIG. 7). A substantially rigid collar 85 is molded on the distal end 84 of the body 72; the collar 85 preferably has a substantially annular shape. The collar 85 defines an opening for allowing a needle 32 on a syringe 10 received in the opening to extend distally beyond the body 72. The distal region 89 of the body 72 comprises a pair of tabs or springboards 86 disposed on the side rails 80 on opposite sides of the body 72 (FIG. 8). The springboards 86 are configured to engage the luer lock 40 and prevent rotation of the luer lock 40 when depressed inwardly as discussed further below. The interior face 87 of the springboards 86 may comprise grooves or other surface features (not shown) to facilitate the engagement with the luer lock 40 or may be substantially flat. The distal region 89 of the body 72 also comprises one or more protrusions 88 designed to engage the proximal end 77 of the spring 76. In a preferred embodiment, the distal region 89 of the body 72 may comprise a pair of distal detents or elongate fingers 122 disposed on opposite sides of the body 72 (FIG. 5). The elongate fingers 122 include end tabs 124 configured to engage a proximal slot 105 disposed on the shield 74 as discussed further below.

The shield 74 is a tubular member adapted to slidably fit on the body 72 and has a proximal end 91 and a distal end 92 (FIG. 7). The shield 74 may comprise opposing side rails 93 defining two elongate openings or windows 94 extending at least partially between the proximal end 91 and the distal end 92 of the shield 74. The proximal end 91 of the shield 74 preferably includes two finger grips or protrusions 95 on opposite sides of the shield 74. The finger grips 95 may facilitate controlling the rate of movement of the needle guard 70 relative to the syringe 10. Alternatively, the shield 74 may include a single finger grip (not shown) that extends around the entire outer periphery or circumference of the proximal end 91 of the shield 74.

Figure 6:
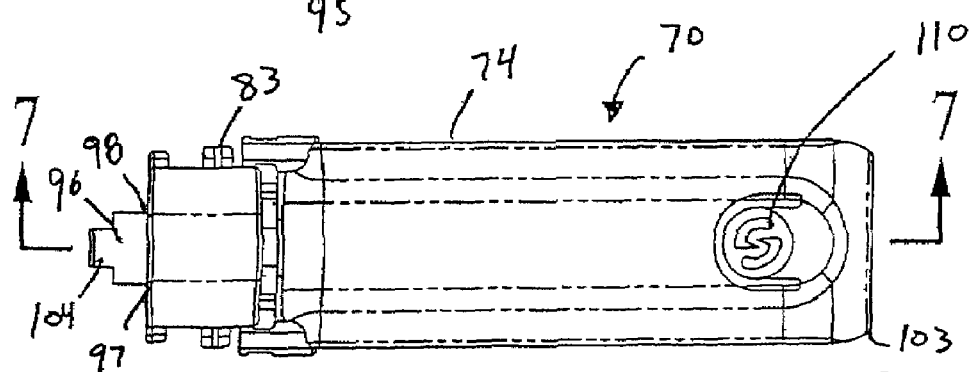
FIG. 6 shows a side view of the needle guard of the present invention.

One or more latch members 96 extend proximally from the proximal end 91 of the shield 74. The latch members 96 may include a first catch 97 that is configured to engage a second catch 98 on the proximal end 83 of the body 72 of the needle guard 70 (FIGS. 5 and 6). Engagement between the first catch 97 and the second catch 98 retains the shield 74 in a first, retracted position. Preferably, the one or more latch members 96 are elongate fingers having a proximal tip 104 that is engageable by a radial element 28 of a plunger 24 as it is depressed to axially compress and deflect the one or more latch members 96 radially outwardly as is discussed further below. The shield 74 further comprises a collar 103 molded on the distal end 92 of the shield 74 (FIG. 7). The collar 103 defines an opening for allowing a needle 32 on a syringe 10 received in the opening to extend distally beyond the shield 74 when the shield 74 is in the first, retracted position (FIG. 8).

In a preferred embodiment, the proximal end 91 of the shield 74 comprises a pair of proximal openings or slots 105 on opposite sides of the shield 74 (FIGS. 5 and 7). The proximal slots 105 are dimensioned to receive the end tabs 124 disposed on the body 72. During administration of the medication to a patient, the passive needle guard 70 transitions from the first, retracted position to a second, extended position. Engagement between the proximal slot 105 and the end tab 124 "locks" the shield 74 in the extended position and prevents retraction of the shield 74 after administration of the medication.

The shield 74 also comprises a pair of anti-rotation tabs 110 located on opposite sides of the shield 74 near the distal end 92 (FIGS. 1-8). When the shield 74 is in the first, retracted position, the anti-rotation tabs 110 are in communication with the springboards 86 located on the body 72 of the passive needle guard 70 (FIG. 8). Inward depression of the anti-rotation tabs 110 by a user during a needle exchange, insertion, or removal creates an inward force on the springboards 86. This inward force causes the springboards 86 to contact the luer lock 40. When sufficient pressure is applied, contact between the springboards 86 and the luer lock 40 restricts the rotation of the luer lock 40. This allows for the exchange, insertion, or removal of a needle 32 using the luer lock 40. Without application of this force to prevent rotation of the luer lock 40, the luer lock 40 would rotate thereby preventing a user from properly inserting and/or removing a needle 32.

The passive needle guard 70 also preferably includes a spring mechanism 76 coupled to the body 72 and the shield 74 for biasing the shield 74 towards the extended position (FIGS. 7-8). The spring mechanism 76 may be a compression spring disposed between the body 72 and the shield 74, for example, disposed concentrically within the shield 74 adjacent to one end of the body 72 or within elongate passages defined by the shield 74 and/or body 72. The shield 74 may be biased by the spring mechanism 76 from the first, or retracted, position wherein the needle 32 of the syringe 10 is exposed, towards the second, extended position wherein the shield 74 covers the needle 32. One or more latch members 96 extend proximally from the shield 74 and are engageable by a radial element 28 of a plunger 24 (FIG. 1). The first catch 97 on the one or more latch members 96 and the second catch 98 on the body 72 of the needle guard 70 act to retain the shield 74 in the first, retracted position (FIG. 6). As the plunger 24 is advanced distally within the syringe 10, the radial element or thumb pad 28 of the plunger 24 may contact the one or more latch members 96 and release the first catch 97 and the second catch 98 whereupon the shield 74 may slide towards the second, extended position. The one or more latch members 96 may include a proximal tip 104 configured for engaging the radial element 28 of the plunger 24 (FIG. 8). Preferably, the needle guard 70 also comprises a pair of cooperating slots 105 and end tabs 124 that retain the shield 74 in the second, extended position (FIGS. 5 and 7). As the shield 74 advances to the extended position, the cooperating end tabs 124 on the body 72 enter into the slots or openings 105 disposed on the shield 74 thereby locking the shield 74 in the extended position. Therefore, once the shield 74 has been triggered to advance to the extended position, the shield 74 may be locked in a distal position thereby preventing reuse of the needle 32, reducing the risk of accidental needle sticks, and/or facilitating the disposal of the syringe 10.

In addition, the passive needle guard 70 may include a locking mechanism on the proximal end of the body, such as one or more locking detents 108 on a finger grip thereof, for substantially securing the syringe 10 in the slot 114 (FIGS. 1 and 7). The locking detents 108 are configured to receive the flange 18 of the syringe 10. To assemble the syringe 10, the distal end 14 of the syringe 10 may be inserted into the proximal end 83 of the body 72 of the needle guard 70. The needle guard 70 may then be moved proximally such that the proximal end 83 of the needle guard 70 is coupled with the proximal end 16 of the syringe 10. The body 72 of the needle guard 70 and the proximal end 16 of the syringe 10 may be secured by the one or more locking detents 108 attached to the proximal end 83 of the body 72 of the needle guard 70. The locking detents 108 may have tapered proximal edges 109, allowing the syringe 10 to be directed further distally, the flange 18 moving the locking detents 108 aside and entering the slot 114 (FIG. 1). The locking detents 108 have substantially blunt distal edges 111 that prevent the syringe 10 from being removed proximally from the slot 114, thereby substantially permanently locking the syringe 10 into the body 72, and preventing axial (i.e. proximal and/or distal) movement of the syringe 10 within the passive needle guard 70.

Figure 2:
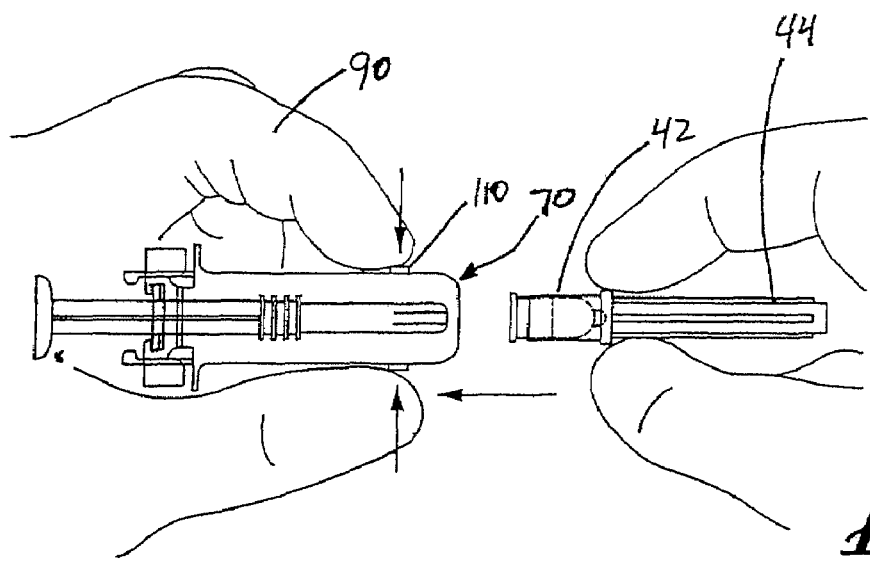
FIGS. 2-4 show a method of using the syringe system of the present invention.
Figure 3:
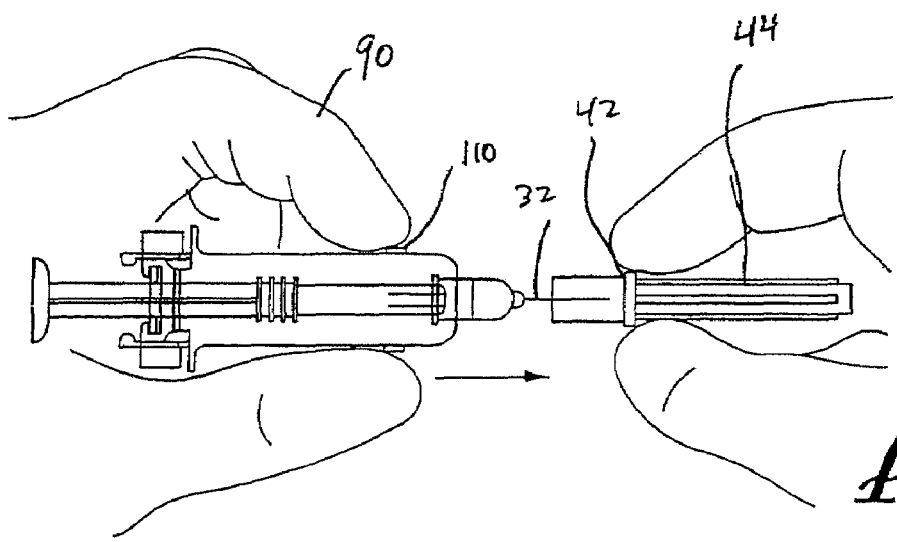

In operation, a syringe 10 mounted in a passive needle guard 70 is provided and a syringe cap 36 is connected to a luer lock 40 (FIG. 1). The passive needle guard comprises a body 72 and a shield 74 and may further comprise a spring mechanism 76. In order to remove the syringe cap 36, a user 90 depresses anti-rotation tabs 110 disposed on the shield 74 of the needle guard 70. The anti-rotation tabs 110 are aligned with springboards 86 disposed on the body 72 when the shield 74 is in the a first, retracted position. Depression of the anti-rotation tabs 110 forces the springboards 86 to contact the luer lock which prevents rotation of the luer lock 40. The user 90 then attaches a luer needle 42 preferably covered with a luer sheath 44 to the luer lock 40 by maintaining pressure on the anti-rotation tabs 110 and screwing the luer needle 42 into the luer lock 40 (FIG. 2). Just prior to administration of the medication, the user 90 removes the needle sheath 44 from the luer needle 42 (FIG. 3).

Figure 4:
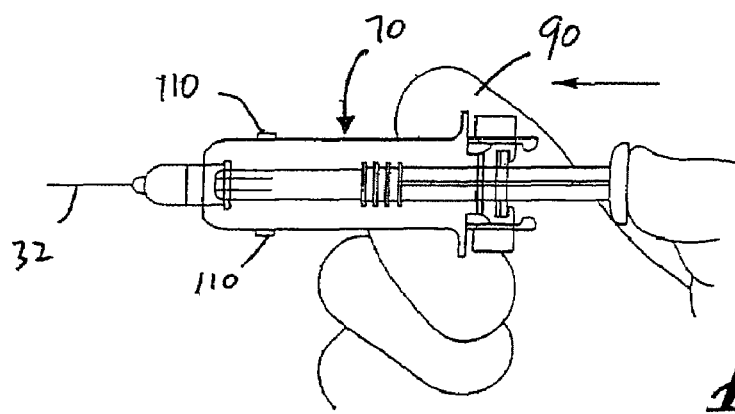

The user 90 then administers the medication to the selected patient by depressing the plunger 24 distally (FIG. 4). Distal depression of the plunger 24 of the syringe 10 activates the passive needle guard 70. One or more latch members 96 of the shield 74 are forced laterally and a first catch 97 and a second catch 98 separate. A spring mechanism 76 then forces the shield 74 of the passive needle guard 70 to a second, extended position. In this extended position, the shield 74 covers the needle 32 thereby preventing needle sticks and/or reuse of the syringe 10. End tabs 124 disposed near the distal end 84 of the body 72 enter into proximal slots 105 on the shield 74 to secure the shield 74 in the extended position.

While the invention is susceptible to various modifications and alternative forms, specific examples thereof have been shown in the drawings and herein described in detail. It should be understood, however, that the invention is not to be limited to the particular forms or methods disclosed, but to the contrary, the intention is to cover all modifications, equivalents, and alternatives falling within the spirit and scope of the appended claims.

The invention claimed is:

1. A syringe system comprising a syringe barrel comprising a proximal end and a distal end, the proximal end configured to receive a plunger and a stopper;
   a luer lock disposed at the distal end of the syringe barrel;
   a needle guard coupled with the syringe barrel, wherein the needle guard comprises a body being configured to receive the syringe barrel and a shield slidable between a retracted position for exposing a needle extending from the distal end of the syringe and an extended position for substantially covering the needle;
   one or more springboards disposed on a distal portion of the body of the needle guard; and
   one or more anti-rotation tabs disposed on a distal portion of the shield of the needle guard;
   wherein the anti-rotation tabs are configured to contact the springboards and the springboards are configured to contact the luer lock to substantially prevent rotation of the luer lock when the anti-rotation tabs are depressed.

2. The syringe system of claim 1 further comprising a spring disposed between the body and the shield for biasing the shield towards the extended position.

3. The syringe system of claim 1 wherein the shield comprises one or more slots disposed on the proximal end of the shield and the body comprises one or more tabs disposed near a distal end, the tabs being configured to enter into the slots when the shield is in the extended position to substantially lock the shield in the extended position.

4. The syringe system of claim 3 wherein the tabs are disposed on the ends of elongate fingers.

5. The syringe system of claim 1 further comprising a luer needle coupled with the luer lock.

* * * * *